United States Patent
Pallem et al.

(10) Patent No.: US 8,809,849 B2
(45) Date of Patent: Aug. 19, 2014

(54) PREPARATION OF CERIUM-CONTAINING PRECURSORS AND DEPOSITION OF CERIUM-CONTAINING FILMS

(71) Applicant: American Air Liquide, Inc., Fremont, CA (US)

(72) Inventors: Venkateswara R. Pallem, Hockessin, DE (US); Christian Dussarrat, Houston, TX (US); Wontae Noh, Houston, TX (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 14/039,692

(22) Filed: Sep. 27, 2013

(65) Prior Publication Data

US 2014/0113456 A1   Apr. 24, 2014

Related U.S. Application Data

(63) Continuation of application No. 13/328,586, filed on Dec. 16, 2011, now abandoned, which is a continuation-in-part of application No. 12/479,175, filed on Jun. 5, 2009, now Pat. No. 8,283,201.

(60) Provisional application No. 61/059,214, filed on Jun. 5, 2008.

(51) Int. Cl.
*H01L 35/24* (2006.01)

(52) U.S. Cl.
USPC ................................. 257/40; 257/E51.001

(58) Field of Classification Search
CPC ............ H01L 51/0545; H01L 51/0541; H01L 51/0036; H01L 51/5012; B82Y 10/00
USPC ............................................. 257/40, E51.001
See application file for complete search history.

(56) References Cited

U.S. PATENT DOCUMENTS

| | | |
|---|---|---|
| 5,453,494 A | 9/1995 | Kirlin et al. |
| 7,396,949 B2 | 7/2008 | Denk et al. |
| 2006/0024443 A1 | 2/2006 | Sakai et al. |
| 2006/0046521 A1 | 3/2006 | Vaartstra et al. |
| 2008/0102205 A1 | 5/2008 | Barry et al. |
| 2008/0305260 A1 | 12/2008 | Shenai-Khatkhate et al. |
| 2009/0302434 A1 | 12/2009 | Pallem et al. |

FOREIGN PATENT DOCUMENTS

| | | |
|---|---|---|
| JP | 2006 37161 | 2/2006 |
| JP | 2006 511716 | 4/2006 |
| WO | WO 2004 046417 | 6/2004 |
| WO | WO 2006 012052 | 2/2006 |
| WO | WO 2008 088563 | 7/2008 |

OTHER PUBLICATIONS

Baunemann, A. et al., "Tantalum complexes with all nitrogen coordination sphere; mixed amido-, imido-, guanidinato complexes of tantalum and their thermal behaviour," The Royal Society of Chemistry, Dalton Trans., 2005, p. 3051-3055.
Elliott, S.D. "Improving ALD growth rate via ligand basicity: Quantum chemical calculations on lanthanum precursors". Surface and Coatings Technology, Elsevier, Amsterdam, NL, vol. 201, No. 22-23, Aug. 9, 2007, pp. 9076-9081: pp. 9079-9080.
Päiväsaari, J. et al. "A comparative study of lanthanide oxide thin films grown by atomic layer deposition". Thin Solid Films, vol. 472, 2005, pp. 275-281: Abstract.
Pi, C. et al. "Multiple N—H bond activation: Synthesis and reactivity of functionalized primary amido ytterbium complexes". Organometallics, vol. 26, 2007, pp. 1934-1946: p. 1944.
Rao V.P. et al., 'Development of lanthanides precursors as dopants for advanced high-k materials Abstract, 218th ECS Meeting, 2010 Electrochemical Society, Las Vegas, Nevada.
Zhang, J. et al., "Insertion of carbodiimide into the Ln—C σ-bond of organolanthanide complexes. Synthesis, reaction, and characterization of organolanthanide amidinates $(C_5H_5)_2Ln['BuN—C(N'Bu)—N'Bu]$ (Ln = Er, Gd, Y)," Organometallics 2002, 21, pp. 1420-1424.
International Search Report and Written Opinion for related PCT/US2009/046443, Oct. 23, 2009.

*Primary Examiner* — Anthony Ho
(74) *Attorney, Agent, or Firm* — Patricia E. McQueeney

(57) ABSTRACT

Methods and compositions for depositing rare earth metal-containing layers are described herein. In general, the disclosed methods deposit the precursor compounds comprising rare earth-containing compounds using deposition methods such as chemical vapor deposition or atomic layer deposition. The disclosed precursor compounds include a cyclopentadienyl ligand having at least one aliphatic group as a substituent and an amidine ligand.

11 Claims, 7 Drawing Sheets

PREPARATION OF CERIUM-CONTAINING PRECURSORS AND DEPOSITION OF CERIUM-CONTAINING FILMS

CROSS REFERENCE TO RELATED APPLICATIONS

The present application is a continuation application of U.S. application Ser. No. 13/328,586 filed Dec. 16, 2011, which is a continuation-in-part application of U.S. application Ser. No. 12/479,175 filed Jun. 5, 2009, which claims the benefit of U.S. Provisional Application Ser. No. 61/059,214 filed Jun. 5, 2008, each of which is incorporated by reference herein in their entireties for all purposes.

BACKGROUND

One of the serious challenges the industry faces is developing new gate dielectric materials for Dynamic Random Access Memory (DRAM) and capacitors. For decades, silicon dioxide ($SiO_2$) was a reliable dielectric, but as transistors have continued to shrink and the technology moved from "Full Si" transistor to "Metal Gate/High-k" transistors, the reliability of the $SiO_2$-based gate dielectric is reaching its physical limits. The need for new high dielectric constant material and processes is increasing and becoming more and more critical as the size for current technology is shrinking. New generations of oxides especially based on lanthanide-containing materials are thought to give significant advantages in capacitance compared to conventional dielectric materials.

Nevertheless, deposition of lanthanide-containing layers is difficult and new material and processes are increasingly needed. For instance, atomic layer deposition (ALD) has been identified as an important thin film growth technique for microelectronics manufacturing, relying on sequential and saturating surface reactions of alternatively applied precursors, separated by inert gas purging. The surface-controlled nature of ALD enables the growth of thin films having high conformality and uniformity with an accurate thickness control. The need to develop new ALD processes for rare earth materials is obvious.

Unfortunately, the successful integration of compounds into deposition processes has proven to be difficult. Two classes of molecules are typically proposed: beta-diketonates and cyclopentadienyls. The former family of compounds is stable, but the melting points always exceed 90° C., making them impractical. Lanthanide 2,2-6,6-tetramethylheptanedionate's [La(tmhd)$_3$] melting point is as high as 260° C., and the related lanthanide 2,2,7-trimethyloctanedionate's [La(tmod)$_3$] melting point is 197° C. Additionally, the delivery efficiency of beta-diketonates is very difficult to control. Non-substituted cyclopentadienyl compounds also exhibit low volatility with a high melting point. Molecule design may both help improve volatility and reduce the melting point. However, in process conditions, these classes of materials have been proven to have limited use. For instance, La(iPrCp)$_3$ does not allow an ALD regime above 225° C.

Some of the lanthanide-containing precursors currently available present many drawbacks when used in a deposition process. For instance, fluorinated lanthanide precursors can generate $LnF_3$ as a by-product. This by-product is known to be difficult to remove.

Consequently, there exists a need for alternate precursors for deposition of lanthanide-containing films.

SUMMARY

Disclosed herein are lanthanide-containing precursors of the general formula:

$$Ln(R^1Cp)_m(R^2-N-C(R^4)=N-R^2)_n,$$

wherein:
Ln=Sc, Y, La, Ce, Pr, Nd, Sm, Eu, Gd, Tb, Dy, Ho, Er, Tm, Yb, Lu;
$R^1$ is selected from the group consisting of H and a C1-C5 alkyl chain;
$R^2$ is selected from the group consisting of H and a C1-C5 alkyl chain;
$R^4$ is selected from the group consisting of H and Me;
n and m range from 1 to 2; and
the precursor has a melting point below approximately 105° C.
the precursor being Ce(iPrCp)$_2$(iPr—N—C(H)=N-iPr).
the precursor being Pr(iPrCp)$_2$(iPr—N—C(H)=N-iPr).

The disclosed lanthanide-containing precursors may optionally include one or more of the following aspects:
Ln being Ce.
Ln being Pr.
Ln being selected from the group consisting of Lu, Gd, Tb, Dy, Ho, Er, Tm, and Yb.
Ln being selected from the group consisting of Er and Yb.
$R^1$ being selected from the group consisting of Me, Et, and iPr.
$R^2$ being selected from the group consisting of iPr and tBu.

Also disclosed is a method for depositing a lanthanide-containing film on a semiconductor substrate, the method comprising:
a) providing a substrate,
b) providing the disclosed lanthanide-containing precursor and
c) depositing a lanthanide-containing film on the substrate.

The disclosed method may optionally include one or more of the following aspects:
depositing the lanthanide-containing film on the substrate at a temperature between about 150° C. and about 600° C.
depositing the lanthanide-containing film on the substrate at a pressure between about 0.5 mTorr and about 20 Torr.
the lanthanide-containing precursor being a liquid at a temperature below 70° C.
the lanthanide-containing precursor being a liquid at a temperature below 40° C.
the lanthanide-containing film being selected from the group consisting of $Ln_2O_3$, $(LnLn')O_3$, $Ln_2O_3$-$Ln'_2O_3$, $LnSi_xO_y$, $LnGe_xO_y$, (Al, Ga, Mn)$LnO_3$, $HfLnO_x$, and $ZrLnO_x$, wherein Ln and Ln' are different.
the lanthanide-containing film being selected from the group consisting of $HfLnO_x$ and $ZrLnO_x$.
the lanthanide-containing precursor having the general formula selected from the group consisting of $Ln(R^1Cp)_2(N^Z\text{-fmd})$, $Ln(R^1Cp)_2(N^Z\text{-amd})$, $Ln(R^1Cp)(N^Z\text{-fmd})_2$, and $Ln(R^1Cp)(N^Z\text{-amd})_2$, wherein $R^1$ is selected from the group consisting of Me, Et, and iPr; and Z is iPr or tBu.
the lanthanide-containing precursor being Ce(iPrCp)$_2$(iPr—N—C(H)=N-iPr).
the lanthanide-containing precursor being Pr(iPrCp)$_2$(iPr—N—C(H)=N-iPr).

Also disclosed is a second method of forming a lanthanide-containing film on a substrate comprising the steps of providing a reactor having at least one substrate disposed therein, introducing at least one lanthanide-containing precursor disclosed herein into the reactor, and contacting the lanthanide-containing precursor and the substrate to form a lanthanide-containing layer on at least one surface of the substrate using a deposition process.

The disclosed second method may optionally include one or more of the following aspects:

- providing at least one oxygen containing fluid into the reactor and reacting the lanthanide-containing precursor with the oxygen containing fluid.
- the oxygen containing fluid being selected from the group consisting of $O_2$, $O_3$, $H_2O$, $H_2O_2$, acetic acid, formalin, para-formaldehyde, and combinations thereof.
- the lanthanide-containing precursor and the reactant species being either introduced at least partially simultaneously as in a chemical vapor deposition process, or are introduced at least partially sequentially as in an atomic layer deposition process.
- introducing a metal precursor into the reactor, wherein the metal precursor is different than the lanthanide-containing precursor, and depositing at least part of the metal precursor to form the lanthanide-containing layer on the one or more substrates.
- a metal of the metal precursor being selected from the group consisting of Hf, Si, Al, Ga, Mn, Ti, Ta, Bi, Zr, Pb, Nb, Mg, Sr, Y, Ba, Ca, a lanthanide, and combinations thereof.
- the deposition process being a chemical vapor deposition process.
- the deposition process being an atomic layer deposition process having a plurality of deposition cycles.
- the lanthanide-containing precursor having the general formula selected from the group consisting of $Ln(R^1Cp)_2(N^Z\text{-fmd})$, $Ln(R^1Cp)_2(N^Z\text{-amd})$, $Ln(R^1Cp)(N^Z\text{-fmd})_2$, and $Ln(R^1Cp)(N^Z\text{-amd})_2$, wherein $R^1$ is selected from the group consisting of Me, Et, and iPr; and Z is iPr or tBu.
- the lanthanide-containing precursor being $Ce(iPrCp)_2$(iPr—N—C(H)=N-iPr).
- the lanthanide-containing precursor being $Pr(iPrCp)_2$(iPr—N—C(H)=N-iPr). Also disclosed are lanthanide-containing film coated substrates comprising the product of the disclosed second method.

NOTATION AND NOMENCLATURE

Certain abbreviations, symbols, and terms are used throughout the following description and claims and include: the abbreviation "Ln" refers to the lanthanide group, which includes the following elements: scandium ("Sc"), yttrium ("Y"), lutetium ("Lu"), lanthanum ("La"), cerium ("Ce"), praseodymium ("Pr"), neodymium ("Nd"), samarium ("Sm"), europium ("Eu"), gadolinium ("Gd"), terbium ("Tb"), dysprosium ("Dy"), holmium ("Ho"), erbium ("Er"), thulium ("Tm"), or ytterbium ("Yb"); the abbreviation "Cp" refers to cyclopentadiene; the abbreviation "Å" refers to angstroms; prime ("'") is used to indicate a different component than the first, for example $(LnLn')O_3$ refers to a lanthanide oxide containing two different lanthanide elements; the term "aliphatic group" refers to a C1-C5 linear or branched chain alkyl group; the term "alkyl group" refers to saturated functional groups containing exclusively carbon and hydrogen atoms; the abbreviation "Me" refers to a methyl group; the abbreviation "Et" refers to an ethyl group; the abbreviation "Pr" refers to a propyl group; the abbreviation "iPr" refers to an isopropyl group; the abbreviation "tBu" refers to a tertiary butyl group, the abbreviation "$N^Z$-amd" refers to $ZNC(CH_3)$=NZ, wherein Z is a defined alkyl group such as iPr or tBu; the abbreviation "$N^Z$-fmd" refers to ZNC(H)=NZ, wherein Z is a defined alkyl group such as iPr or tBu; the abbreviation "CVD" refers to chemical vapor deposition; the abbreviation "LPCVD" refers to low pressure chemical vapor deposition; the abbreviation "ALD" refers to atomic layer deposition; the abbreviation "P-CVD" refers to pulsed chemical vapor deposition; the abbreviation "PE-ALD" refers to plasma enhanced atomic layer deposition; the abbreviation "MIM" refers to Metal Insulator Metal (a structure used in capacitors); the abbreviation "DRAM" refers to dynamic random access memory; the abbreviation "FeRAM" refers to ferroelectric random access memory; the abbreviation "CMOS" refers to complementary metal-oxide-semiconductor; the abbreviation "THF" refers to tetrahydrofuran; the abbreviation "TGA" refers to thermogravimetric analysis; the abbreviation "TMA" refers to trimethyl aluminum; the abbreviation "TBTDET" refers to tertiary butylimido, tris(diethylamino) tantalum $(Ta[N(C_2H_5)_2]_3[NC(CH_3)_3])$; the abbreviation "TAT-DMAE" refers to tantalum tetraethoxide dimethylaminoethoxide; the abbreviation "PET" refers to pentaethoxy tantalum; the abbreviation "TBTDEN" refers to tertiary butylimido, tris(diethylamino)niobium; the abbreviation "PEN" refers to pentaethoxy niobium; the abbreviation "TriDMAS" refers to tris(dimethylamino)silane $[SiH(NMe_2)_3]$; the abbreviation "BDMAS" refers to bis(dimethylamino) silane; the abbreviation "BDEAS" refers to bis(diethylamino)silane $[SiH_2(NEt_2)_2]$; the abbreviation "TDEAS" refers to tetrakis-diethylamino silane; the abbreviation "TDMAS" refers to tris(dimethylamino)silane; the abbreviation "TEMAS" refers to tetrakis-ethylmethylamino silane $(Si(N(C_2H_5)(CH_3))_4)$; the abbreviation "BTBAS" refers to bis(tert-butylamino)silane $[SiH_2(NHtBu)_2]$.

BRIEF DESCRIPTION OF THE DRAWINGS

For a further understanding of the nature and objects of the present invention, reference should be made to the following detailed description, taken in conjunction with the accompanying drawings, wherein.

DESCRIPTION OF PREFERRED EMBODIMENTS

Figure 1:
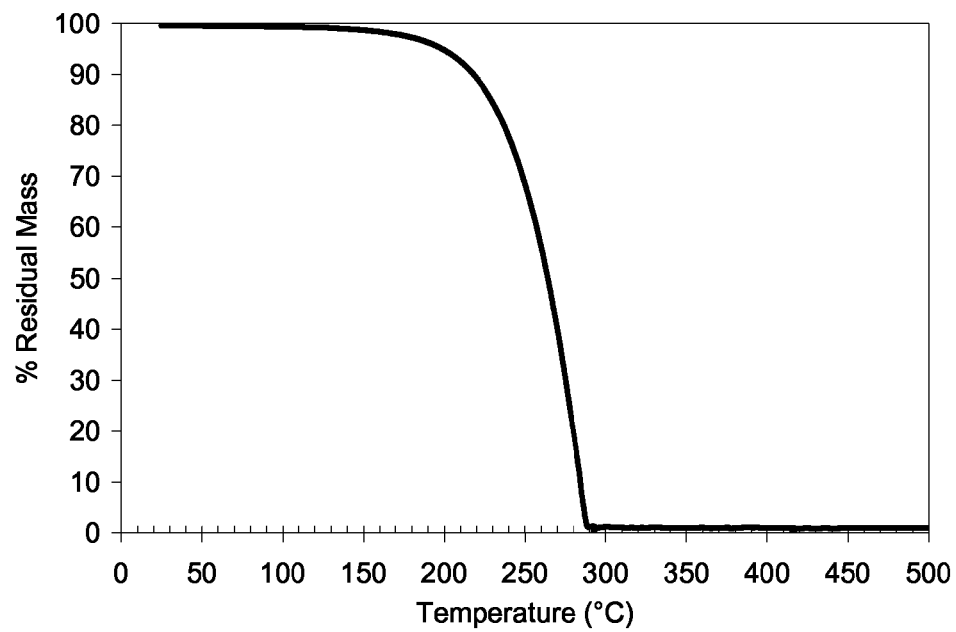
FIG. 1 is a TGA graph demonstrating the percentage of weight loss with temperature change of $Y(MeCp)_2(N^{iPr}\text{-amd})$.

Disclosed are lanthanide-containing precursor compounds having the general formula:

$Ln(R^1Cp)_m(R^2—N—C(R^4)=N—R^2)_n$, wherein Ln represents the lanthanide group, which includes Sc, Y, La, Ce, Pr, Nd, Sm, Eu, Gd, Tb, Dy, Ho, Er, Tm, Yb, Lu; $R^1$ is selected from H or a C1-C5 alkyl chain; $R^2$ is selected from H or a C1-C5 alkyl chain; $R^4$ is selected from H or a C1-C5 alkyl chain; m is selected from 1 or 2; and n is selected from 1 or 2.

The lanthanide-containing precursors offer unique physical and chemical properties when compared to their corresponding homoleptic compounds, which include tris-substituted cyclopentadienyl lanthanide compounds, $Ln(RCp)_3$, tris-acetamidinate compounds, $Ln(R—N—C(R')=N—R)_3$, or tris-formamidinate compounds, $Ln(R—N—C(H)=N—R)_3$. Such properties include better control of steric crowding around the metal center, which in turn controls the surface reaction on the substrate and the reaction with a second reactant (such as an oxygen source). Independently fine tuning the substituents on the ligands increases volatility and thermal stability and decreases melting point to yield either liquids or low melting solids (having a melting point below approximately 105° C.).

In order to synthesize stable lanthanide-containing precursors with properties suited for the vapor deposition process (i.e., a volatile, yet thermally stable, liquid or low melting solid (having a melting point below about 105° C.)), a direct correlation between the properties of the central metal ion (coordination number) and ligands (steric effect, ratio of two heteroleptic ligands) has been observed. Preferably, the metal compound has a 3+ charge and coordination number of 6. As a result, Ln is preferably Ce. Preferably $R^1$ is a C1-C3 alkyl chain; $R^2$ is a C3-C4 alkyl chain, and $R^4$ is H or Me. Preferably the lanthanide-containing precursor has a melting point below about 105° C., preferably below about 80° C., more preferably below about 70° C., and even more preferably below about 40° C. Preferred lanthanide-containing precursors include $Ln(R^1Cp)_2(N^Z\text{-fmd})$, $Ln(R^1Cp)_2(N^Z\text{-amd})$, $Ln(R^1Cp)(N^Z\text{-fmd})_2$, and $Ln(R^1Cp)(N^Z\text{-amd})_2$, wherein $R^1$ is Me, Et, or iPr; and Z is iPr or tBu.

The synthesis of the $Ln(R^1Cp)_m(R^2—N—C(R^4)=N—R^2)_n$ precursor (where m=2, n=1 or m=1, n=2) may be carried out by following methods:

Method A
By reacting $Ln(R^1Cp)_2X$ (where X=Cl, Br or I) with $M(R^2—N—C(R^4)=N—R^2)$ (where M=Li, Na, K) or by reacting $Ln(R^1Cp)X_2$ with $2M(R^2—N—C(R^4)=N—R^2)$ (Scheme-1).

Scheme-1

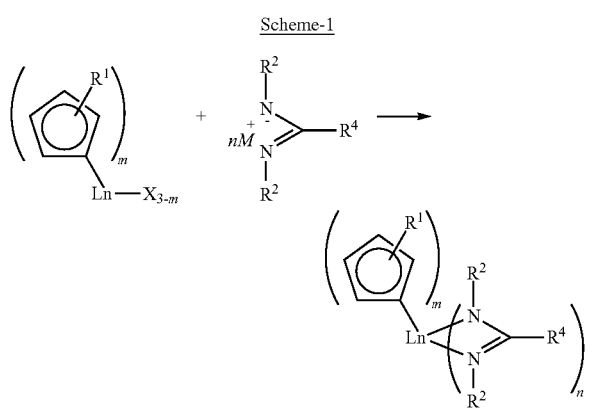

Method B

By reacting $Ln(R^1Cp)_3$ with one equivalent of amidine/guanidine, $R^2—NH—C(R^4)=N—R^2$, to yield $Ln(R^1Cp)_2(R^2—N—C(R^4)=N—R^2)$ or with two equivalents of amidine/guanidine, $R^2—NH—C(R^4)=N—R^2$, to yield $Ln(R^1Cp)(R^2—N—C(R^4)=N—R^2)_2$ (Scheme-2).

Scheme-2

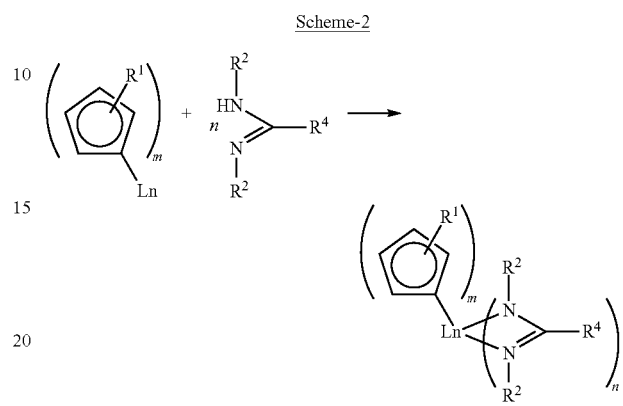

Method C
In-situ reacting $LnX_3$ (where X=Cl, Br, I) (in a stepwise reaction without isolation of intermediate products) with $mR^1CpM$ (where M=Li, Na, K) followed by filtration, and reacting the filtrate with $nM(R^2—N—C(R^4)=N—R^2)$ to result in $Ln(R^1Cp)_m(R^2—N—C(R^4)=N—R^2)_n$ precursor (Scheme-3).

Scheme-3

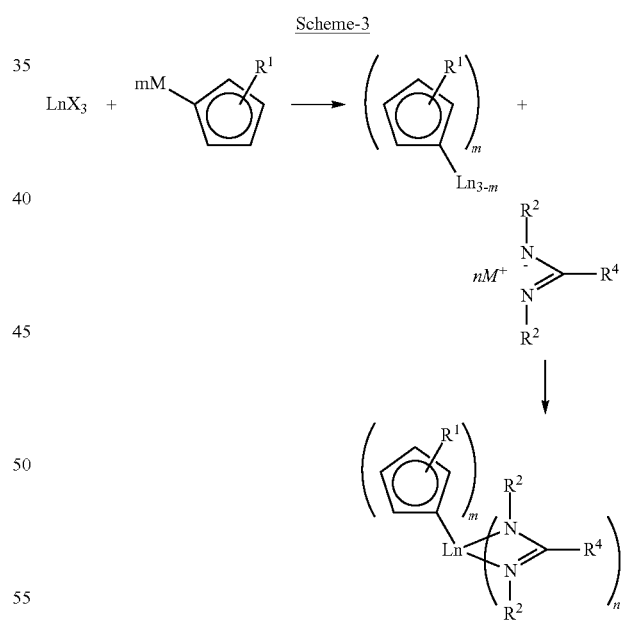

The disclosed precursor compounds (hereinafter the "lanthanide-containing precursor") may be deposited to form lanthanide-containing films using any deposition methods known to those of skill in the art. Examples of suitable deposition methods include without limitation, conventional chemical vapor deposition (CVD), low pressure chemical vapor deposition (LPCVD), atomic layer deposition (ALD), pulsed chemical vapor deposition (P-CVD), plasma enhanced atomic layer deposition (PE-ALD), or combinations thereof.

The type of substrate upon which the lanthanide-containing film will be deposited will vary depending on the final use intended. In some embodiments, the substrate may be chosen from oxides which are used as dielectric materials in MIM, DRAM, FeRam technologies or gate dielectrics in CMOS technologies (for example, $HfO_2$ based materials, $TiO_2$ based materials, $ZrO_2$ based materials, rare earth oxide based materials, ternary oxide based materials, etc.) or from nitride-based films (for example, TaN) that are used as an oxygen barrier between copper and the low-k layer. Other substrates may be used in the manufacture of semiconductors, photovoltaics, LCD-TFT, or flat panel devices. Examples of such substrates include, but are not limited to, solid substrates such as metal substrates (for example, Au, Pd, Rh, Ru, W, Al, Ni, Ti, Co, Pt and metal silicides, such as $TiSi_2$, $CoSi_2$, and $NiSi_2$); metal nitride containing substrates (for example, TaN, TiN, WN, TaCN, TiCN, TaSiN, and TiSiN); semiconductor materials (for example, Si, SiGe, GaAs, InP, diamond, GaN, and SiC); insulators (for example, $SiO_2$, $Si_3N_4$, SiON, $HfO_2$, $Ta_2O_5$, $ZrO_2$, $TiO_2$, $Al_2O_3$, and barium strontium titanate); or other substrates that include any number of combinations of these materials. The actual substrate utilized may also depend upon the specific precursor embodiment utilized. In many instances though, the preferred substrate utilized will be selected from TiN, Ru, and Si type substrates.

The lanthanide-containing precursor is introduced into a reaction chamber containing at least one substrate. The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems.

The reaction chamber may be maintained at a pressure ranging from about 0.5 mTorr to about 20 Torr. In addition, the temperature within the reaction chamber may range from about 250° C. to about 600° C. One of ordinary skill in the art will recognize that the temperature may be optimized through mere experimentation to achieve the desired result.

The substrate may be heated to a sufficient temperature to obtain the desired lanthanide-containing film at a sufficient growth rate and with desired physical state and composition. A non-limiting exemplary temperature range to which the substrate may be heated includes from 150° C. to 600° C. Preferably, the temperature of the substrate remains less than or equal to 450° C.

The lanthanide-containing precursor may be fed in liquid state to a vaporizer where it is vaporized before it is introduced into the reaction chamber. Prior to its vaporization, the lanthanide-containing precursor may optionally be mixed with one or more solvents, one or more metal sources, and a mixture of one or more solvents and one or more metal sources. The solvents may be selected from the group consisting of toluene, ethyl benzene, xylene, mesitylene, decane, dodecane, octane, hexane, pentane, or others. The resulting concentration may range from approximately 0.05 M to approximately 2 M. The metal source may include any metal precursors now known or later developed.

Alternatively, the lanthanide-containing precursor may be vaporized by passing a carrier gas into a container containing the lanthanide-containing precursor or by bubbling the carrier gas into the lanthanide-containing precursor. The carrier gas and lanthanide-containing precursor are then introduced into the reaction chamber. If necessary, the container may be heated to a temperature that permits the lanthanide-containing precursor to be in its liquid phase and to have a sufficient vapor pressure. The carrier gas may include, but is not limited to, Ar, He, $N_2$, and mixtures thereof. The lanthanide-containing precursor may optionally be mixed in the container with a solvent, another metal precursor, or a mixture thereof. The container may be maintained at temperatures in the range of, for example, 0-100° C. Those skilled in the art recognize that the temperature of the container may be adjusted in a known manner to control the amount of lanthanide-containing precursor vaporized.

In addition to the optional mixing of the lanthanide-containing precursor with solvents, metal precursors, and stabilizers prior to introduction into the reaction chamber, the lanthanide-containing precursor may be mixed with reactant species inside the reaction chamber. Exemplary reactant species include, without limitation, $H_2$, metal precursors such as TMA or other aluminum-containing precursors, other lanthanide-containing precursors, TBTDET, TAT-DMAE, PET, TBTDEN, PEN, and any combination thereof.

When the desired lanthanide-containing film also contains oxygen, such as, for example and without limitation, erbium oxide, the reactant species may include an oxygen source which is selected from, but not limited to, $O_2$, $O_3$, $H_2O$, $H_2O_2$, acetic acid, formalin, para-formaldehyde, and combinations thereof.

When the desired lanthanide-containing film also contains nitrogen, such as, for example and without limitation, erbium nitride or erbium carbo-nitride, the reactant species may include a nitrogen source which is selected from, but not limited to, nitrogen ($N_2$), ammonia and alkyl derivatives thereof, hydrazine and alkyl derivatives thereof, N-containing radicals (for instance N., NH., $NH_2$.), NO, $N_2O$, $NO_2$, amines, and any combination thereof.

When the desired lanthanide-containing film also contains carbon, such as, for example and without limitation, erbium carbide or erbium carbo-nitride, the reactant species may include a carbon source which is selected from, but not limited to, methane, ethane, propane, butane, ethylene, propylene, t-butylene, isobutylene, $CCl_4$, and any combination thereof.

When the desired lanthanide-containing film also contains silicon, such as, for example and without limitation, erbium silicide, erbium silico-nitride, erbium silicate, erbium silico-carbo-nitride, the reactant species may include a silicon source which is selected from, but not limited to, $SiH_4$, $Si_2H_6$, $Si_3H_8$, TriDMAS, BDMAS, BDEAS, TDEAS, TDMAS, TEMAS, $(SiH_3)_3N$, $(SiH_3)_2O$, trisilylamine, disiloxane, trisilylamine, disilane, trisilane, an alkoxysilane $SiH_x(OR^1)_{4-x}$, a silanol $Si(OH)_x(OR^1)_{4-x}$ (preferably $Si(OH)(OR^1)_3$; more preferably $Si(OH)(OtBu)_3$ an aminosilane $SiH_x(NR^1R^2)_{4-x}$ (where x is 1, 2, 3, or 4; $R^1$ and $R^2$ are independently H or a linear, branched or cyclic C1-C6 carbon chain; preferably TriDMAS, BTBAS, and/or BDEAS), and any combination thereof. The targeted film may alternatively contain Germanium (Ge), in which case the above-mentioned Si-containing reactant species could be replaced by Ge-containing reactant species.

When the desired lanthanide-containing film also contains another metal, such as, for example and without limitation, Ti, Ta, Hf, Zr, Nb, Mg, Al, Sr, Y, Ba, Ca, As, Sb, Bi, Sn, Pb, or combinations thereof, the reactant species may include a metal source which is selected from, but not limited to, metal alkyls such as $SbR^{i'}_3$ or $SnR^{i'}_4$ (wherein each $R^{i''}$ is independently H or a linear, branched, or cyclic C1-C6 carbon chain), metal alkoxides such as $Sb(OR^i)_3$ or $Sn(OR^i)_4$ (where each $R^i$ is independently H or a linear, branched, or cyclic C1-C6 carbon chain), and metal amines such as $Sb(NR^1R^2)(NR^3R^4)(NR^5R^6)$ or $Ge(NR^1R^2)(NR^3R^4)(NR^5R^6)(NR^7R^8)$ (where each $R^1$, $R^2$, $R^3$, $R^4$, $R^5$, $R^6$, $R^7$, and $R^8$ is independently H, a C1-C6 carbon chain, or a trialkylsilyl group, the carbon chain and trialkylsilyl group each being linear, branched, or cyclic), and any combination thereof.

The lanthanide-containing precursor and one or more reactant species may be introduced into the reaction chamber simultaneously (chemical vapor deposition), sequentially (atomic layer deposition), or in other combinations. For example, the lanthanide-containing precursor may be introduced in one pulse and two additional metal sources may be introduced together in a separate pulse [modified atomic layer deposition]. Alternatively, the reaction chamber may already contain the reactant species prior to introduction of the lanthanide-containing precursor. The reactant species may be passed through a plasma system localized remotely from the reaction chamber, and decomposed to radicals. Alternatively, the lanthanide-containing precursor may be introduced to the reaction chamber continuously while other metal sources are introduced by pulse (pulsed-chemical vapor deposition). In each example, a pulse may be followed by a purge or evacuation step to remove excess amounts of the component introduced. In each example, the pulse may last for a time period ranging from about 0.01 s to about 10 s, alternatively from about 0.3 s to about 3 s, alternatively from about 0.5 s to about 2 s.

In one non-limiting exemplary atomic layer deposition type process, the vapor phase of a lanthanide-containing precursor is introduced into the reaction chamber, where it is contacted with a suitable substrate. Excess lanthanide-containing precursor may then be removed from the reaction chamber by purging and/or evacuating the reactor. An oxygen source is introduced into the reaction chamber where it reacts with the absorbed lanthanide precursor in a self-limiting manner. Any excess oxygen source is removed from the reaction chamber by purging and/or evacuating the reaction chamber. If the desired film is a lanthanide oxide film, this two-step process may provide the desired film thickness or may be repeated until a film having the necessary thickness has been obtained.

Alternatively, if the desired film is a lanthanide metal oxide film, the two-step process above may be followed by introduction of the vapor of a metal precursor into the reaction chamber. The metal precursor will be selected based on the nature of the lanthanide metal oxide film being deposited and may include a different lanthanide-containing precursor. After introduction into the reaction chamber, the metal precursor is contacted with the substrate. Any excess metal precursor is removed from the reaction chamber by purging and/or evacuating the reaction chamber. Once again, an oxygen source may be introduced into the reaction chamber to react with the second metal precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the lanthanide-containing precursor, metal precursor, and oxygen source, a film of desired composition and thickness can be deposited.

The lanthanide-containing films or lanthanide-containing layers resulting from the processes discussed above may include $Ln_2O_3$, $(LnLn')O_3$, $Ln_2O_3$-$Ln'_2O_3$, $LnSi_xO_y$, $LnGe_xO_y$, $(Al, Ga, Mn)LnO_3$, $HfLnO_x$ or $ZrLnO_x$. Preferably, the lanthanide-containing film may include $HfErO_x$, $ZrErO_x$, $HfYbO_x$, or $ZrYbO_x$. One of ordinary skill in the art will recognize that by judicial selection of the appropriate lanthanide-containing precursor and reactant species, the desired film composition may be obtained.

EXAMPLES

The following non-limiting examples are provided to further illustrate embodiments of the invention. However, the examples are not intended to be all inclusive and are not intended to limit the scope of the inventions described herein.

Example 1

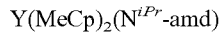
$Y(MeCp)_2(N^{iPr}\text{-amd})$ $N^{iPr}$-amd-Li was prepared by reacting di-isopropylcarbodiimide (4.47 g, 35.36 mmol) in 30 mL of THF at −78° C. by slowly adding 22.1 mL (35.36 mmol) of MeLi ether solution (1.6 M). The solution was stirred at −78° C. for 30 minutes, then warmed to room temperature and further stirred at room temperature for 2 hours. The entire quantity of the freshly prepared $N^{iPr}$-amd-Li solution was added to a flask containing $Y(MeCp)_2Cl$ (10.00 g, 35.38 mmol) in 50 mL of THF. The resulting mixture was stirred overnight. The mixture was evaporated to dryness under vacuum. Pentane was added and stirred, followed by filtration through a column of Celite brand diatomaceous earth. The pentane solvent was evaporated to dryness under vacuum to obtain a pale yellow waxy solid. The pale yellow waxy solid was sublimed at 115° C. at 14 mTorr to produce 12.24 g, which correlates to an 89% yield. The pale yellow waxy solid melted at 30° C. and left a 1% residual mass during TGA analysis measured at a temperature rising rate of 10° C./min in an atmosphere which flows nitrogen at 180 mL/min. These results are depicted in FIG. 1, which is a TGA graph demonstrating the percentage of weight loss with temperature change.

Example 2

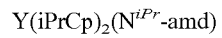
$Y(iPrCp)_2(N^{iPr}\text{-amd})$

Figure 2:
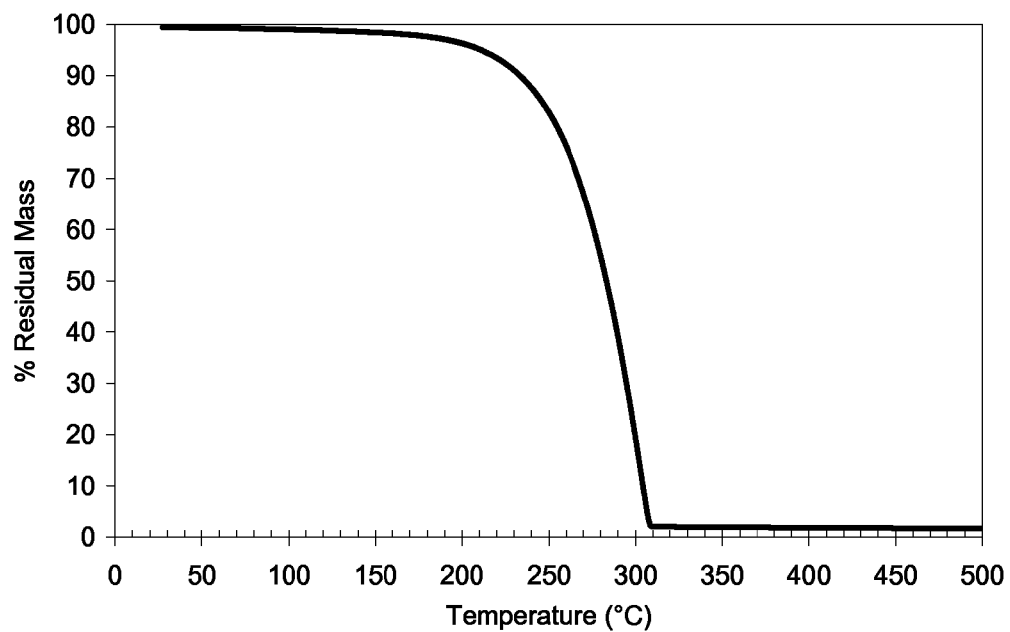
FIG. 2 is a TGA graph for $Y(iPrCp)_2(N^{iPr}\text{-amd})$.

To a flask containing $Y(MeCp)_3$ (11.11 g, 27.07 mmol) in 60 mL of pentane, was added a solution of $N^{iPr}$-amd-H (3.85 g, 27.07 mmol) in 20 mL of pentane. The resulting mixture was stirred overnight. Solvents and volatiles were evaporated under vacuum. The resulting yellow liquid was distilled at 20° C. at 8 mTorr. Yield is 11.4 g (87%). The yellow liquid left a 1% residual mass during TGA analysis measured at a temperature rising rate of 10° C./min in an atmosphere which flows nitrogen at 180 mL/min. These results are depicted in FIG. 2, which is a TGA graph demonstrating the percentage of weight loss with temperature change.

Example 3

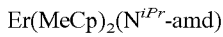
$Er(MeCp)_2(N^{iPr}\text{-amd})$

Figure 3:
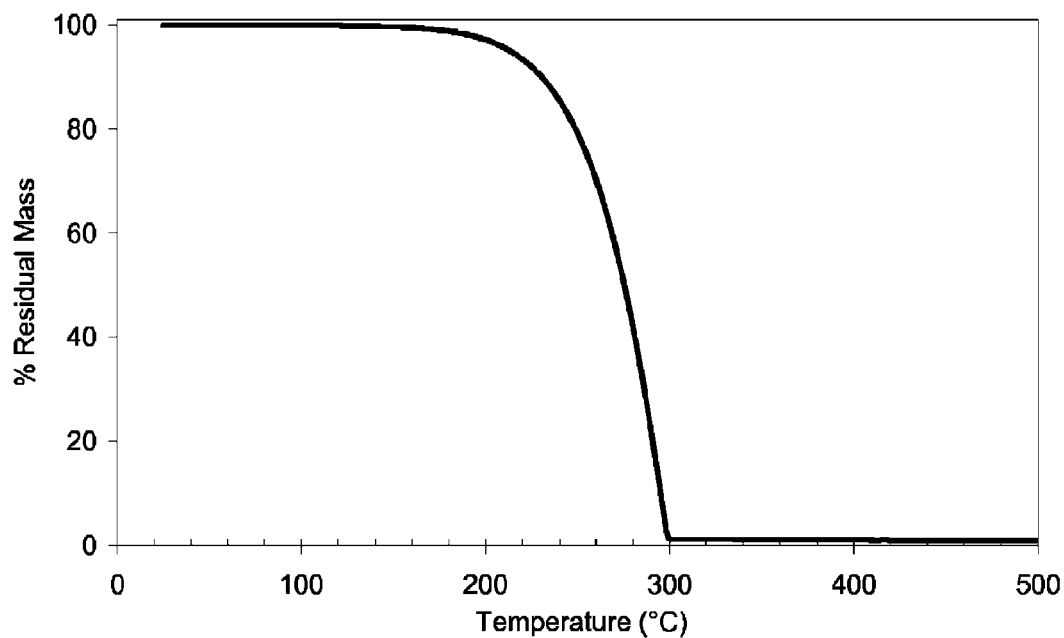
FIG. 3 is a TGA graph for $Er(MeCp)_2$(iPr—N—C(Me)=N-iPr).

A solution of $N^{iPr}$-amd-Li was prepared by reacting di-isopropylcarbodiimide (10.65 g, 84.36 mmol) in 150 mL of THF at −78° C. by slowly adding 53 mL (84.36 mmol) of MeLi ether solution (1.6 M). The solution was stirred at −78° C. for 30 min, then warmed to room temperature and further stirred at room temperature for 2 hours. The entire quantity of freshly prepared $N^{iPr}$-amd-Li solution was added to a flask containing $Er(MeCp)_2Cl$ (30.45 g, 83.36 mmol) in 250 mL of THF. The resulting mixture was stirred overnight. The mixture was evaporated to dryness under vacuum. Pentane was added and stirred, followed by filtration through a column of Celite brand diatomaceous earth. The pentane solvent was evaporated to dryness under vacuum to obtain a pink solid. The pink solid was sublimed at 95-115° C. at 12 mTorr to produce 34.3 g, which correlates to 87% yield. The pink solid melted at 36° C. and left a 2.5% residual mass during TGA analysis measured at a temperature rising rate of 10° C./min in an atmosphere which flows nitrogen at 180 mL/min. These results are depicted in FIG. 3, which is a TGA graph demonstrating the percentage of weight loss with temperature change.

Example 4

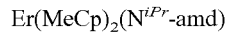
Er(MeCp)$_2$(N$^{iPr}$-amd)

To a flask containing Er(MeCp)$_3$ (11.54 g, 28.12 mmol) in 60 mL of pentane, was added a solution of N$^{iPr}$-amd-H (4.00 g, 128.12 mmol) in 20 mL of pentane. The resulting mixture was stirred overnight. Solvents and volatiles were evaporated under vacuum. The resulting pink solid was distilled at 95-115° C. at 12 mTorr. Yield was 11.4 g (87%).

Example 5

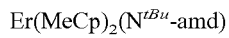
Er(MeCp)$_2$(N$^{tBu}$-amd)

Figure 4:
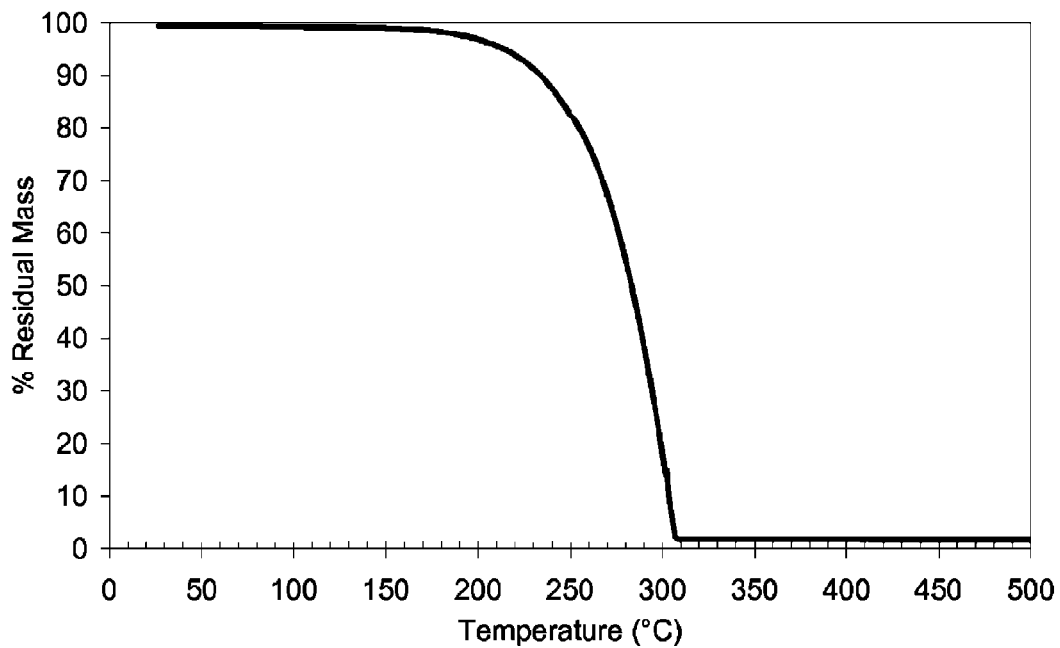
FIG. 4 is a TGA graph for $Er(MeCp)_2$(tBu-N—C(Me)=N-tBu).

A solution of N$^{tBu}$-amd-Li was prepared by reacting 1,3-di-tert-butylcarbodiimide (1.28 g, 8.31 mmol) in 30 mL of THF at −78° C. by slowly adding 5.2 mL (8.31 mmol) of MeLi ether solution (1.6 M). The solution was stirred at −78° C. for 30 minutes, then warmed to room temperature and further stirred at room temperature for 2 hours. The entire quantity of freshly prepared N$^{tBu}$-amd-Li solution was added to a flask containing Er(MeCp)$_2$Cl (3.00 g, 8.31 mmol) in 25 mL of THF. The resulting mixture was stirred overnight. The mixture was evaporated to dryness under vacuum. Pentane was added and stirred, followed by filtration through a column of Celite brand diatomaceous earth. The pentane solvent was evaporated to dryness under vacuum to obtain an orange solid. The orange solid was sublimed at 100-150° C. at 10 mTorr to produce 2.61 g, which correlates to a 64% yield. The orange solid melted at 100° C. and left a 1.8% residual mass during TGA analysis measured at a temperature rising rate of 10° C./min in an atmosphere which flows nitrogen at 180 mL/min. These results are depicted in FIG. 4, which is a TGA graph demonstrating the percentage of weight loss with temperature change.

Example 6

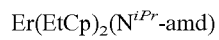
Er(EtCp)$_2$(N$^{iPr}$-amd)

Figure 5:
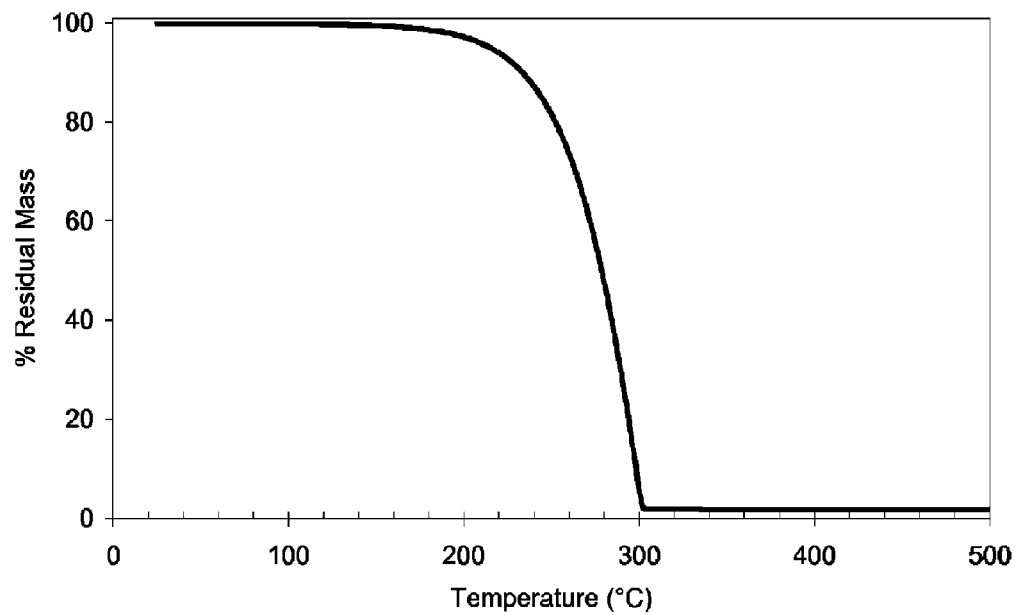
FIG. 5 is a TGA graph for $Er(EtCp)_2$(iPr—N—C(Me)=N-iPr).

To a flask containing Er(EtCp)$_3$ (20.00 g, 44.77 mmol) in 200 mL of pentane, was added a solution of N$^{iPr}$-amd-H (6.37 g, 44.77 mmol) in 50 mL of pentane. The resulting mixture was stirred overnight. Solvents and volatiles were evaporated under vacuum. The resulting pink liquid was distilled at 72-74° C. at 8 mTorr. Yield is 16.4 g (67%). The melting point was 18° C. The pink liquid left a 2% residual mass during TGA analysis measured at a temperature rising rate of 10° C./min in an atmosphere which flows nitrogen at 180 mL/min. These results are depicted in FIG. 5, which is a TGA graph demonstrating the percentage of weight loss with temperature change.

Example 7

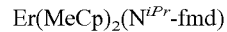
Er(MeCp)$_2$(N$^{iPr}$-fmd)

Figure 6:
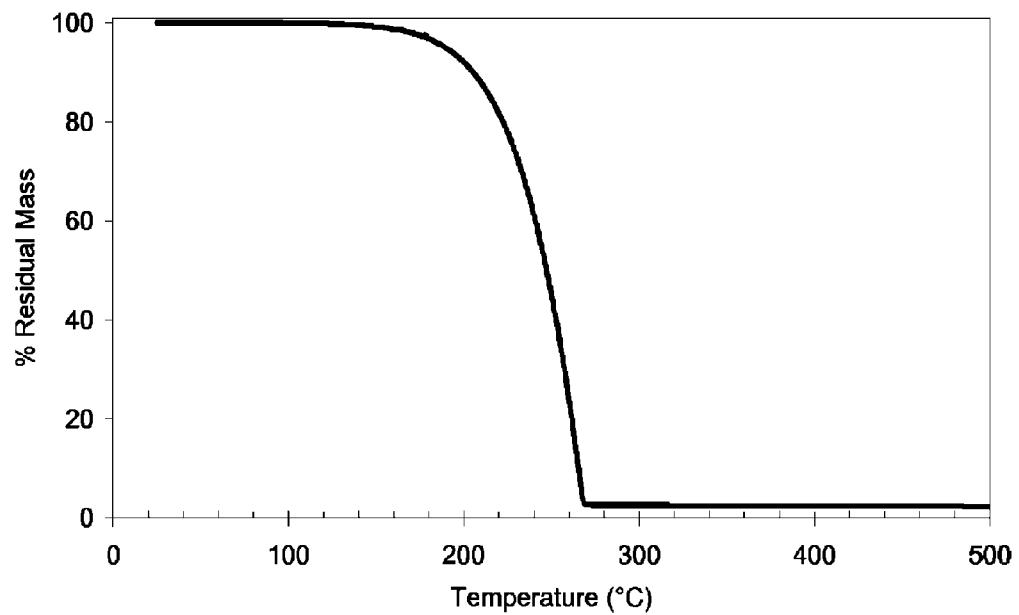
FIG. 6 is a TGA graph for $Er(MeCp)_2$(iPr—N—C(H)=N-iPr).

A solution of N$^{iPr}$-fmd-Li was prepared by reacting di-isopropylformamidine (10.00 g, 7.80 mmol) in 40 mL of THF at −78° C. by slowly adding 4.9 mL (7.80 mmol) of MeLi ether solution (1.6 M). The solution was stirred at −78° C. for 30 minutes, then warmed to room temperature and further stirred at room temperature for 2 hours. The entire quantity of the freshly prepared N$^{iPr}$-fmd-Li solution was added to a flask containing Er(MeCp)$_2$Cl (2.81 g, 7.80 mmol) in 50 mL of THF. The resultant mixture was stirred overnight. The mixture was evaporated to dryness under vacuum. Pentane was added and stirred, followed by filtration through a column of Celite brand diatomaceous earth. The pentane solvent was evaporated to dryness under vacuum to obtain a pink solid. The pink solid was sublimed at 60-80° C. at 3 mTorr to obtain 2.2 g, which correlated to a 62% yield. The pink solid melted at 50° C. and left a 5% residual mass during TGA analysis measured at a temperature rising rate of 10° C./min in an atmosphere which flows nitrogen at 180 mL/min. These results are depicted in FIG. 6, which is a TGA graph demonstrating the percentage of weight loss with temperature change.

Example 8

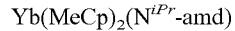
Yb(MeCp)$_2$(N$^{iPr}$-amd)

Figure 7:
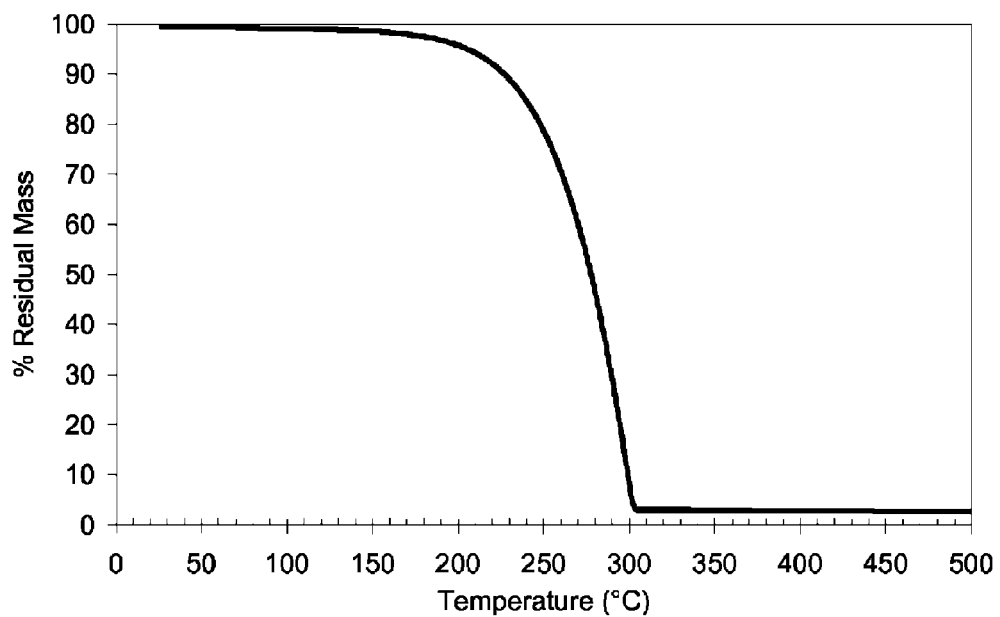
FIG. 7 is a TGA graph for $Yb(MeCp)_2$(iPr—N—C(Me)=N-iPr).

A solution of N$^{iPr}$-amd-Li was prepared by reacting di-isopropylcarbodiimide (6.88 g, 54.54 mmol) in 100 mL of THF at −78° C. by slowly adding 34.1 mL (54.54 mmol) of MeLi ether solution (1.6 M). The solution was stirred at −78° C. for 30 minutes, then warmed to room temperature and further stirred at room temperature for 2 hours. The entire quantity of freshly prepared N$^{iPr}$-amd-Li solution was added to a flask containing Yb(MeCp)$_2$Cl (20.00 g, 54.54 mmol) in 120 mL of THF. The resultant mixture was stirred overnight. The mixture was evaporated to dryness under vacuum. Pentane was added and stirred, followed by filtration through a column of Celite brand diatomaceous earth. The pentane solvent was evaporated to dryness under vacuum to obtain an orange solid. The orange solid was sublimed at 120° C. at 25 mTorr to produce 22.4 g, which correlates to an 87% yield. The orange solid melted at 36° C. and left a 3% residual mass during TGA analysis measured at a temperature rising rate of 10° C./min in an atmosphere which flows nitrogen at 180 mL/min. These results are depicted in FIG. 7, which is a TGA graph demonstrating the percentage of weight loss with temperature change.

Example 9

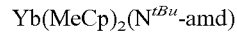
Yb(MeCp)$_2$(N$^{tBu}$-amd)

Figure 8:
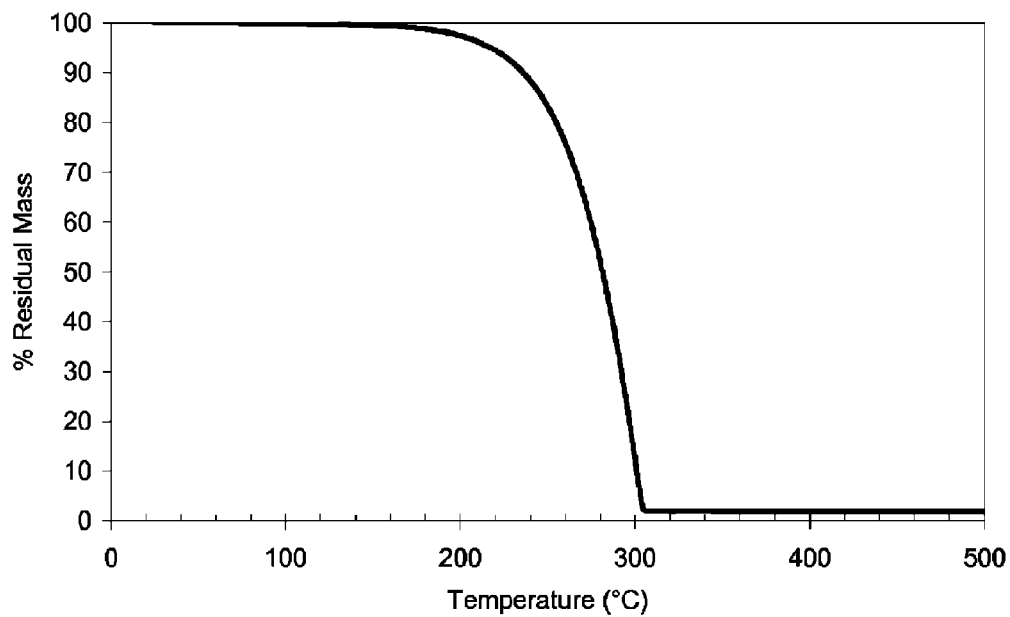
FIG. 8 is a TGA graph for $Yb(MeCp)_2$(tBu-N—C(Me)=N-tBu).

A solution of N$^{tBu}$-amd-Li was prepared by reacting 1,3-di-tert-butylcarbodiimide (1.26 g, 8.18 mmol) in 30 mL of THF at −78° C. by slowly adding 5.1 mL (8.18 mmol) of MeLi ether solution (1.6 M). The solution was stirred at −78° C. for 30 minutes, then warmed to room temperature and further stirred at room temperature for 2 hours. The entire quantity of freshly prepared N$^{tBu}$-amd-Li solution was added to a flask containing Yb(MeCp)$_2$Cl (3.00 g, 8.18 mmol) in 25 mL of THF. The resulting mixture was stirred overnight. The mixture was evaporated to dryness under vacuum. Pentane was added and stirred, followed by filtration through a column of Celite brand diatomaceous earth. The pentane solvent was evaporated to dryness under vacuum to obtain an orange solid. The orange solid was sublimed at 125° C. at 10 mTorr to produce 1.73 g, which correlates to a 43% yield. The orange solid melted at 103° C. and left a 1.8% residual mass during TGA analysis measured at a temperature rising rate of 10° C./min in an atmosphere which flows nitrogen at 180 mL/min. These results are depicted in FIG. 8, which is a TGA graph demonstrating the percentage of weight loss with temperature change.

Example 10

Yb(EtCp)$_2$(N$^{iPr}$-amd)

Figure 9:
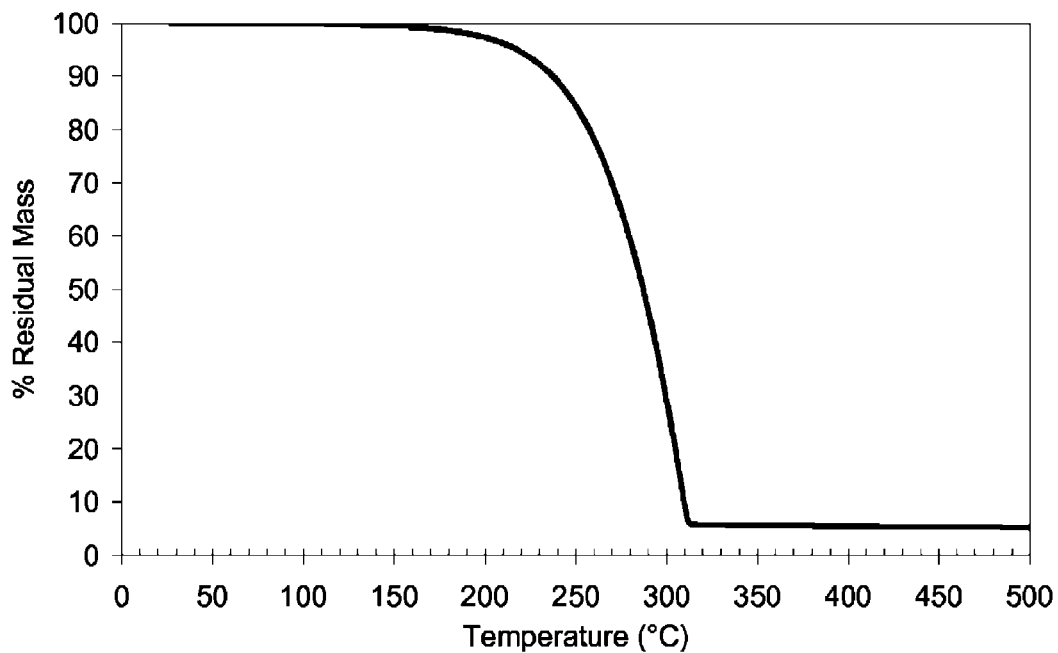
FIG. 9 is a TGA graph for $Yb(EtCp)_2$(iPr—N—C(Me)=N-iPr).

To a flask containing Yb(EtCp)$_3$ (15.90 g, 35.15 mmol) in 250 mL of pentane, was added a solution of N$^{iPr}$-amd-H (5.00 g, 35.15 mmol) in 40 mL of pentane. The resulting mixture was stirred overnight. Solvents and volatiles were evaporated under vacuum. The resulting orange liquid was distilled at 110° C. at 10 mTorr. Yield is 15.00 g (85%). The melting point was 39° C. The orange liquid left a 3.5% residual mass during TGA analysis measured at a temperature rising rate of 10° C./min in an atmosphere which flows nitrogen at 180 mL/min. These results are depicted in FIG. 9, which is a TGA graph demonstrating the percentage of weight loss with temperature change.

Example 11

Yb(EtCp)$_2$(N$^{iPr}$-fmd)

Figure 10:
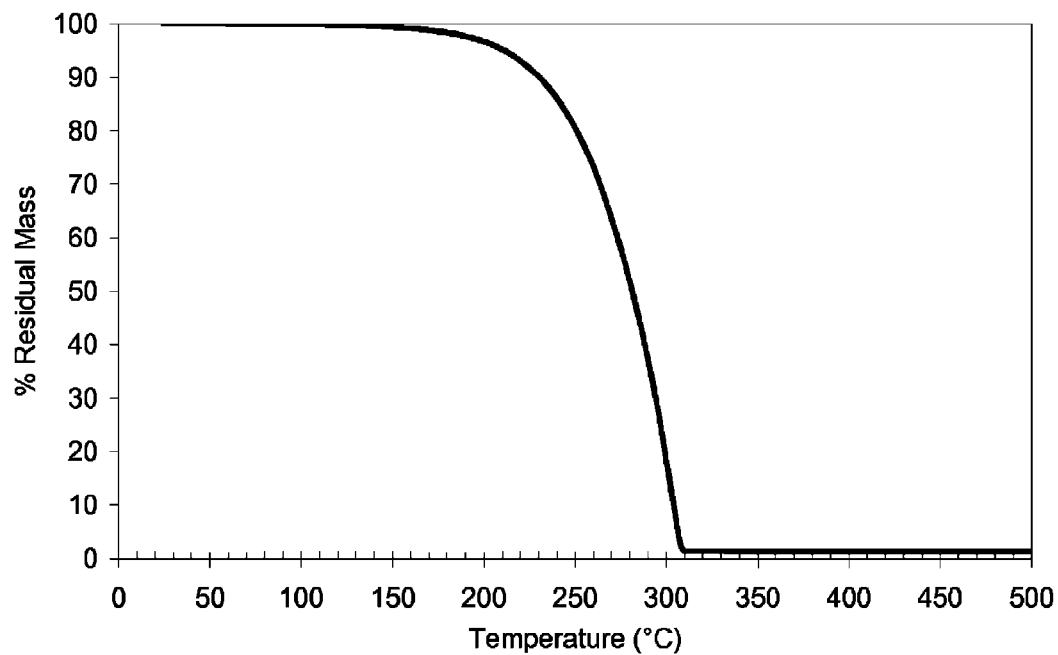
FIG. 10 is a TGA graph for $Yb(EtCp)_2$(iPr—N—C(H)=N-iPr).

To a flask containing Yb(EtCp)$_3$ (6.00 g, 13.26 mmol) in 20 mL of toluene, was added slowly a solution of N$^{iPr}$-fmd-H (1.7 g, 13.26 mmol) in 20 mL of toluene. The resulting mixture was stirred overnight. Solvents and volatiles were evaporated under vacuum. The resulting orange liquid was distilled at 120° C. at 6 mTorr. Yield is 5.9 g (97%). The orange liquid left a 1.4% residual mass during TGA analysis measured at a temperature rising rate of 10° C./min in an atmosphere which flows nitrogen at 180. These results are depicted in FIG. 10, which is a TGA graph demonstrating the percentage of weight loss with temperature change.

Example 12

Yb(iPrCp)$_2$(N$^{iPr}$-fmd)

Figure 11:
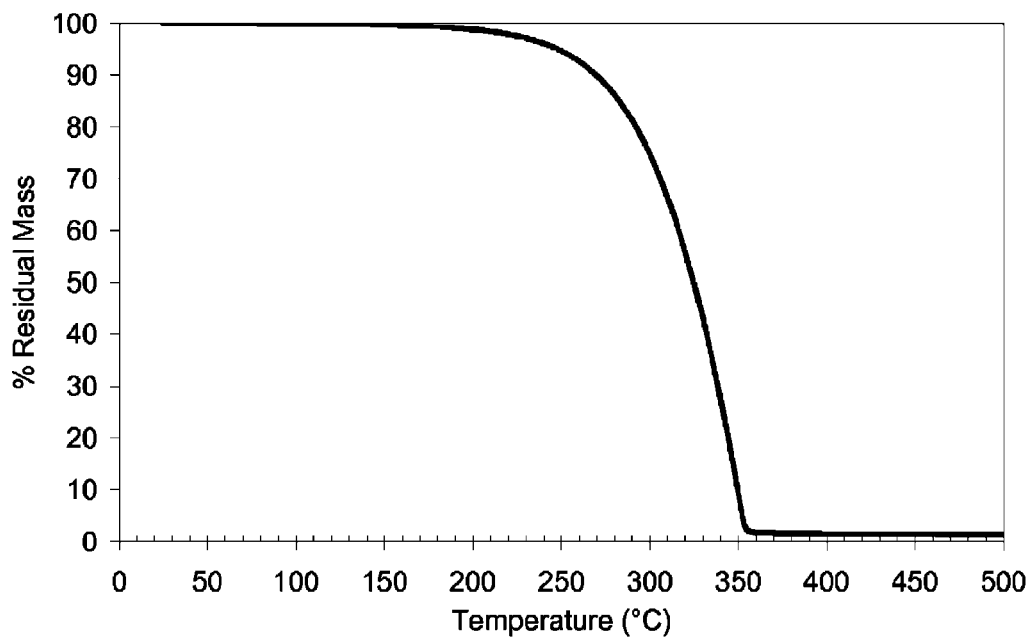
FIG. 11 is a TGA graph for $Yb(iPrCp)_2$(iPr—N—C(H)=N-iPr).

To a flask containing Yb(EtCp)$_3$ (3.00 g, 6.07 mmol) in 20 mL of toluene, was added slowly a solution of N$^{iPr}$-fmd-H (0.78 g, 6.07 mmol) in 20 mL of toluene. The resulting mixture was stirred overnight. Solvents and volatiles were evaporated under vacuum. The resulting orange liquid was distilled at 140° C. at 20 mTorr. Yield is 2.5 g (80%). The orange liquid left a 2% residual mass during TGA analysis measured at a temperature rising rate of 10° C./min in an atmosphere which flows nitrogen at 180 mL/min. These results are depicted in FIG. 11, which is a TGA graph demonstrating the percentage of weight loss with temperature change.

Example 13

Er(MeCp)$_2$(iPr—N—C(Me)=N-iPr)

The lanthanide-containing precursor of Example 3, Er(MeCp)$_2$(iPr—N—C(Me)=N-iPr), and the reactant O$_3$ were used to deposit a film of Er$_2$O$_3$ on a SiO$_2$/Si substrate. The SiO$_2$/Si substrate was maintained at a temperature of 275° C. The pink solid precursor was vaporized in a bubbler maintained at 115° C. The ALD cycle included a precursor pulse of 10 seconds, followed by a 5 second purge, followed by a reactant pulse of 2 seconds, followed by a 5 second purge. The Er$_2$O$_3$ growth rate was observed to be 1.2 Å/cycle. The ALD regime was assessed up to 275° C. with a deposition rate as high as 1.2 Å/cycle.

Example 14

Er(EtCp)$_2$(iPr—N—C(Me)=N-iPr)

The lanthanide-containing precursor of Example 6, Er(EtCp)$_2$(iPr—N—C(Me)=N-iPr), and the reactant O$_3$ were used to deposit a film of Er$_2$O$_3$ on a SiO$_2$/Si substrate. The SiO$_2$/Si substrate was maintained at a temperature of 250° C. The pink liquid precursor was vaporized in a bubbler maintained at 115° C. The ALD cycle included a precursor pulse of 10 seconds, followed by a 5 second purge, followed by a reactant pulse of 2 seconds, followed by a 5 second purge. The Er$_2$O$_3$ growth rate was observed to be 0.3 Å/cycle. The ALD regime was assessed up to 275° C. with a deposition rate as high as 0.3 Å/cycle.

Example 15

Yb(MeCp)$_2$(iPr—N—C(Me)=N-iPr)

The lanthanide-containing precursor of Example 8, Yb(MeCp)$_2$(iPr—N—C(Me)=N-iPr), and the reactant H$_2$O were used to deposit a film of Yb$_2$O$_3$ on a SiO$_2$/Si substrate. The SiO$_2$/Si substrate was maintained at a temperature of 250° C. The orange solid precursor was vaporized in a bubbler maintained at 115° C. The ALD cycle included a precursor pulse of 3 seconds, followed by a 5 second purge, followed by a reactant pulse of 2 seconds, followed by a 10 second purge. The Yb$_2$O$_3$ growth rate was observed to be 1.0 Å/cycle. The ALD regime was assessed up to 275° C. with a deposition rate as high as 1.0 Å/cycle.

Example 16

Yb(EtCp)$_2$(iPr—N—C(Me)=N-iPr)

The lanthanide-containing precursor of Example 10, Yb(EtCp)$_2$(iPr—N—C(Me)=N-iPr), and the reactant H$_2$O were used to deposit a film of Yb$_2$O$_3$ on a SiO$_2$/Si substrate. The SiO$_2$/Si substrate was maintained at a temperature of 250° C. The orange liquid precursor was vaporized in a bubbler maintained at 115° C. The ALD cycle included a precursor pulse of 10 seconds, followed by a 5 second purge, followed by a reactant pulse of 2 seconds, followed by a 10 second purge. The Yb$_2$O$_3$ growth rate was observed to be 1.0 Å/cycle. The ALD regime was assessed up to 250° C. with a deposition rate as high as 1.0 Å/cycle.

Example 17

Ce(iPrCp)$_2$(iPr—N—C(H)=N-iPr)

Step 1: A 500 mL Schlenk flask was charged with CeCl$_3$ (9.91 g, 40.21 mmol) and 100 mL THF. The mixture was stirred at Room Temperature (RT) for 5 hours to form a thick oily suspension. In a separate 500 mL Schlenk flask, Na(iPrCp) (10.60 g, 81.44 mmol) was dissolved in 150 mL THF to produce a dark pink solution. The Na(iPrCp) solution was added to the CeCl₃.THF$_x$ suspension at RT dropwise. The resulting yellow, cloudy mixture was stirred overnight at RT to give a green mixture.

Step 2: A 200 mL Shlenk flask and a 150 mL graduated dropping funnel were assembled. iPr—N=C=N-iPr (6.3 mL, 40.69 mmol) was charged to the Schlenk flask and followed by 100 mL of THF. To the iPr—N=C=N-iPr solution in a dry ice bath was added dropwise 27 mL of MeLi (1.6 M in diethyl ether) from the dropping funnel over 30 mins. The resulting yellowish solution was brought to RT and stirred for 3 hrs.

The flask contents of Step 2 were transferred to step 1's flask by a cannula at room temperature. The mixture was stirred overnight to become orange solution. The solvent was evaporated by vacuum and concentrated to about 30% of the original volume. ca. 300 mL of pentane was added and the mixture was stirred RT. The stirring was stopped and the precipitate was settled down to give a yellowish precipitate and a deep red pentane solution. The red solution layer was filtered by a filter cannula. The filtrate was concentrated to ca. 50 mL. The resulting solution was transferred to a 50 mL flask with a 14/20 joint. A distillation head and a receiver were installed onto the flask. Solvents and volatiles were evaporated under vacuum at 50° C. The resulting deep red oil was vacuum distilled at 130-133° C. at 35-40 mTorr. Yield is 7.8 g (39%).

Figure 12:
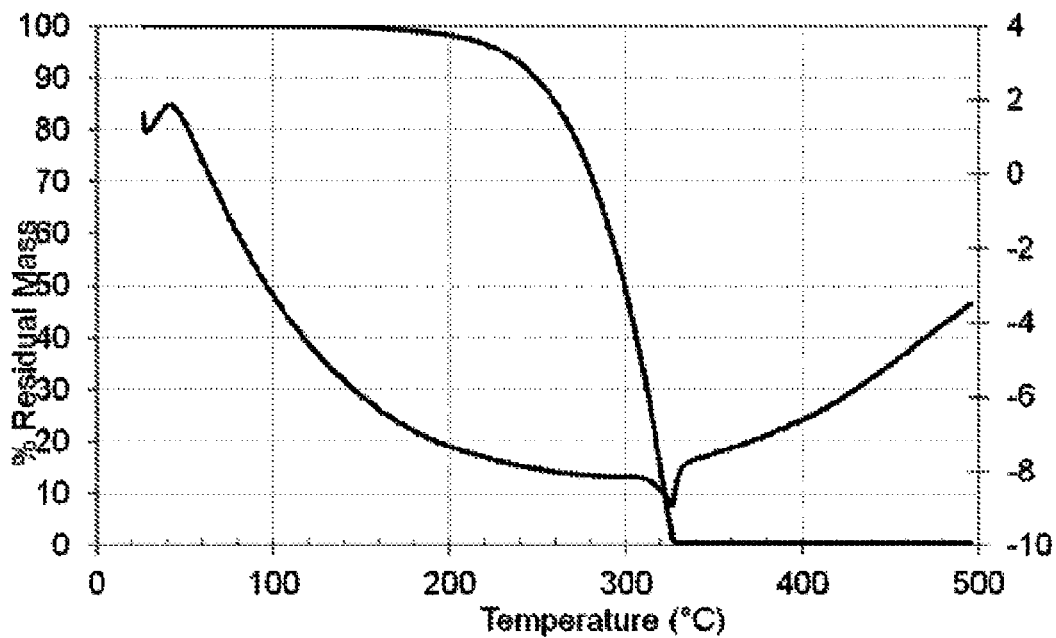
FIG. 12 is a TGA graph for $Ce(iPrCp)_2$(iPr—N—C(H)=N-iPr).

The deep red oil left a <1% residual mass during TGA analysis measured at a temperature rising rate of 10° C./min in an atmosphere which flows nitrogen at 180 mL/min. These results are depicted in FIG. 12, which is a TGA graph demonstrating the percentage of weight loss with temperature change.

Example 18

Pr(iPrCp)₂(iPr—N—C(H)=N-iPr)

To a flask containing Pr(iPrCp)₃ (5.00 g, 10.8 mmol) in 60 mL of toluene, was added a solution of N$^{iPr}$-amd-H (1.54 g, 10.8 mmol) in 20 mL of toluene. The resulting mixture was refluxed while stirring for 8 h. Reaction mixture was cooled to room temperature. Solvents and volatiles were evaporated under vacuum. The resulting green liquid was distilled at 125-140° C. at 50-55 mTorr. Yield is 3.5 g (68%).

Figure 13:
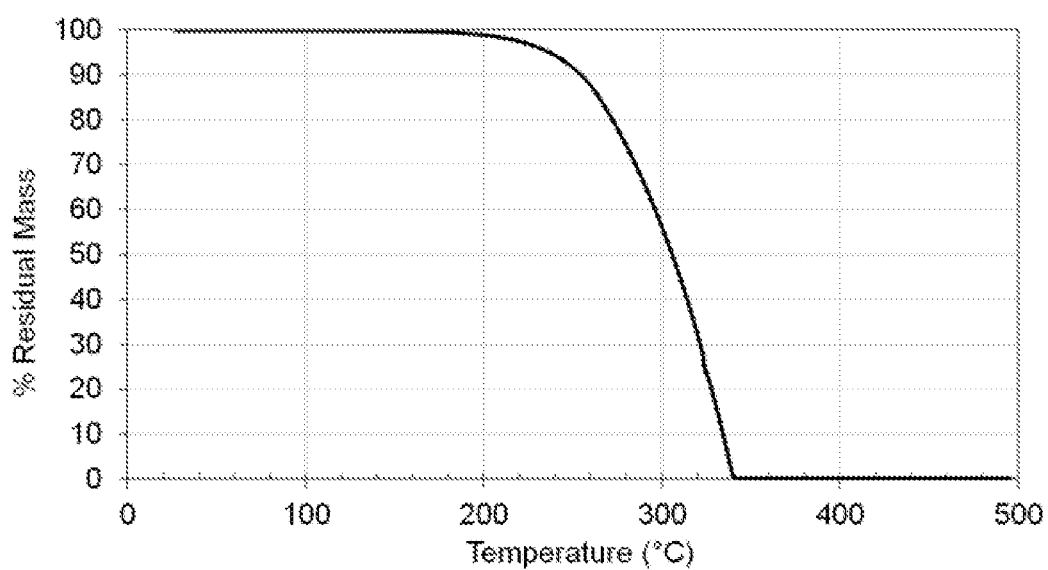
FIG. 13 is a TGA graph for $Pr(iPrCp)2$(iPr—N—C(H)+N-iPr).

The green liquid left a <1% residual mass during TGA analysis measured at a temperature rising rate of 10° C./min in an atmosphere which flows nitrogen at 180 mL/min. These results are depicted in FIG. 13, which is a TGA graph demonstrating the percentage of weight loss with temperature change.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A lanthanide-containing precursor having the general formula:

Ln(R¹Cp)$_m$(R²—N—C(R⁴)=N—R²)$_n$, wherein:
Ln=Sc, Y, La, Ce, Pr, Nd, Sm, Eu, Gd, Tb, Dy, Ho, Er, Tm, Yb, Lu;
R¹ is selected from the group consisting of H and a C1-C5 alkyl chain;
R² is selected from the group consisting of H and a C1-C5 alkyl chain;
R⁴ is selected from the group consisting of H and Me;
n and m range from 1 to 2; and
the precursor has a melting point below approximately 105° C.

2. The composition of claim 1, wherein Ln is Ce.
3. The composition of claim 2, wherein m is 2 and n is 1.
4. The composition of claim 3, wherein R¹ is selected from the group consisting of Me, Et, and iPr.
5. The composition of claim 4, wherein R² is selected from the group consisting of iPr and tBu.
6. The composition of claim 5, wherein R⁴ is Me.
7. The composition of claim 4, wherein R² is iPr.
8. The composition of claim 4, wherein R⁴ is Me.
9. The composition of claim 3, wherein R¹ is iPr.
10. The composition of claim 9, wherein R² is iPr.
11. The composition of claim 3, wherein R⁴ is Me.

* * * * *